(12) United States Patent
Richardson

(10) Patent No.: US 11,918,272 B2
(45) Date of Patent: Mar. 5, 2024

(54) WIRELESSLY CONTROLLED BIPOLAR SURGICAL CAUTERY APPARATUS

(71) Applicant: BILLINGS CLINIC, Bililngs, MT (US)

(72) Inventor: Marlin Dustin Richardson, Billings, MT (US)

(73) Assignee: Billings Clinic, Billings, MT (US)

(*) Notice: Subject to any disclaimer, the term of this patent is extended or adjusted under 35 U.S.C. 154(b) by 188 days.

(21) Appl. No.: 17/208,929

(22) Filed: Mar. 22, 2021

(65) Prior Publication Data

US 2021/0290290 A1 Sep. 23, 2021

Related U.S. Application Data

(60) Provisional application No. 62/992,377, filed on Mar. 20, 2020.

(51) Int. Cl.
| | | |
|---|---|---|
| *A61B 18/12* | (2006.01) | |
| *A61B 18/08* | (2006.01) | |
| *A61B 17/00* | (2006.01) | |
| *A61B 18/00* | (2006.01) | |
| *A61B 18/14* | (2006.01) | |

(52) U.S. Cl.
CPC ........ *A61B 18/085* (2013.01); *A61B 18/1206* (2013.01); *A61B 2017/00221* (2013.01); *A61B 2018/00595* (2013.01); *A61B 2018/00767* (2013.01); *A61B 2018/00928* (2013.01); *A61B 2018/126* (2013.01); *A61B 2018/1462* (2013.01)

(58) Field of Classification Search
CPC ........ A61B 2018/00928; A61B 18/085; A61B 18/1206; A61B 2017/00221; A61B 2018/00595; A61B 2018/00767; A61B 2018/126; A61B 2018/1462
See application file for complete search history.

(56) References Cited

U.S. PATENT DOCUMENTS

| | | | | |
|---|---|---|---|---|
| 5,928,227 A | * | 7/1999 | Howard, III | ........... A61B 18/00 341/176 |
| 6,156,028 A | * | 12/2000 | Prescott | ............... A61N 5/0616 36/43 |
| 6,551,312 B2 | | 4/2003 | Zhang | |
| 8,709,009 B2 | | 4/2014 | Hamel | |
| 9,833,294 B2 | | 12/2017 | Franjic | |
| 10,080,554 B2 | | 9/2018 | Hamel | |
| 2004/0214690 A1 | * | 10/2004 | Couvillion, Jr. | ........ G09B 19/00 482/8 |
| 2008/0140058 A1 | * | 6/2008 | Gassner | ................... G05G 1/42 606/1 |
| 2011/0144636 A1 | | 6/2011 | Alexander | |
| 2012/0186101 A1 | | 7/2012 | Sanchez | |

(Continued)

*Primary Examiner* — Sean W Collins
(74) *Attorney, Agent, or Firm* — Shane P. Coleman

(57) ABSTRACT

A surgical cautery device includes a voltage generator, a controller, forceps, an actuator, and a receiver. The voltage generator is configured to be electrically connected to a power source. The forceps are electrically coupled to the voltage generator and configured to cauterize tissue. The actuator is configured to generate and wirelessly transmit an on/off signal. The receiver is operable to wirelessly receive the on/off signal. The controller controls power to the voltage generator from the power source in response to the on/off signal.

19 Claims, 7 Drawing Sheets

(56) References Cited

U.S. PATENT DOCUMENTS

| | | | | |
|---|---|---|---|---|
| 2012/0232547 A1* | 9/2012 | Cohen | ............... | A61B 18/1492 606/34 |
| 2015/0342667 A1* | 12/2015 | Cornacchia | ........ | A61B 18/1206 606/51 |
| 2022/0160416 A1* | 5/2022 | Smith | ................... | A61B 18/00 |

* cited by examiner

WIRELESSLY CONTROLLED BIPOLAR SURGICAL CAUTERY APPARATUS

CROSS-REFERENCE TO RELATED APPLICATION

This is application claims priority to U.S. Patent Application No. 62/992,377, filed 20 Mar. 2020, and entitled WIRELESSLY CONTROLLED BIPOLAR SURGICAL CAUTERY DEVICE, the disclosure of which is incorporated herein in its entirety by this reference.

TECHNICAL FIELD

The present disclosure relates generally to surgical cautery devices, and more particularly to wirelessly controlled surgical cautery devices, such as bipolar surgical cautery devices, and related methods of use.

BACKGROUND

Cautery devices have been used in surgical procedures to perform cutting and coagulation of tissue and blood vessels. Cauterization of tissue can be used in surgeries, emergency circumstances, etc. to stop bleeding, prevent infections, and minimize potential medical harm. Accordingly, cauterization can play an important role in a number of potentially life threatening situations.

Typically, cautery devices are pen- or tweezer-like devices that a surgeon can grasp by the hand to use. The cautery device is connected to an electrical generator that outputs a level of current that is conducted to a tip of the device to achieve the desired cutting and/or coagulation effect during a surgical procedure. The surgeon controls on/off delivery of current to the cautery device using a foot pedal positioned below the operating table. The foot pedal is unique to bipolar electrosurgery; monopolar electrosurgery mounts the switch on the pencil instrument because the surgeon can operate it with his/her hand.

During some procedures, the surgeon moves around the operating table, and someone is required to reposition the foot pedal where the surgeon can reach it as he/she moves around. It is common for some surgeons to stand on one or more cushioned floor mats in the operating room.

SUMMARY

The present disclosure is directed to a surgical cautery device that includes a voltage generator, a controller, forceps, an actuator, and a receiver. The voltage generator is configured to be electrically connected to a power source. The forceps are electrically coupled to the voltage generator and configured to cauterize tissue. The actuator is configured to generate and wirelessly transmit an on/off signal. The receiver is operable to wirelessly receive the on/off signal. The controller controls power to the voltage generator from the power source in response to the on/off signal.

The actuator may be an on/off switch. The actuator may be embedded in a shoe. The actuator may be embedded in a removable shoe insole. The actuator may be embedded in a floor mat. The on/off signal may be transmitted using one of BLUETOOTH®, Wi-Fi or RFID wireless communication. The surgical cautery device may further include a housing, and the voltage generator and controller are positioned in the housing. The receiver may be positioned in a power cable that extends from the power source to the voltage generator.

Another aspect of the present disclosure relates to a surgical cautery device that includes a controller, forceps configured to cauterize tissue, an actuator configured to wirelessly transmit an on/off signal, and a receiver operable to wirelessly receive the on/off signal. The controller controls power to the forceps in response to the on/off signal.

The actuator may be positioned in a user's shoe and operable by movement of the user's toe. The actuator may be positioned in a floor mat. The surgical cautery device may further include a voltage generator, the forceps being electrically coupled to the voltage generator, and the controller controlling the voltage generator to control power to the forceps.

Another aspect of the present disclosure relates to a surgical cautery device that includes a controller, forceps configured to cauterize tissue, and an actuator configured to transmit a control signal, the actuator being positioned in a user's shoe and operable with a portion of the user's foot. The controller receives the control signal from the actuator and controls power to the forceps in response to the control signal.

The actuator may transmit the control signal wirelessly, and the controller may receive the control signal wirelessly. The actuator may transmit the control signal using one of BLUETOOTH®, Wi-Fi or RFID wireless communication. The surgical cautery device may further include a voltage generator, the forceps being electrically coupled to the voltage generator, and the controller may control the voltage generator to control power to the forceps.

A further aspect of the present disclosure relates to a method of operating a surgical cautery device. The method includes providing the surgical cauterizing device with forceps, a controller and an actuator, actuating the actuator to create a control signal, wirelessly transmitting the control signal to the controller, and controlling power supply to the forceps based on the control signal.

The actuator may be positioned in a user's shoe, and actuating the actuator may include manipulating a portion of the user's foot. The actuator may be positioned in a floor mat, and actuating the actuator may include manipulating a portion of a user's foot that is supported on the floor mat. The surgical cauterizing device may further include a voltage generator, and controlling the power supply to the forceps may include operating the voltage generator with the controller

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
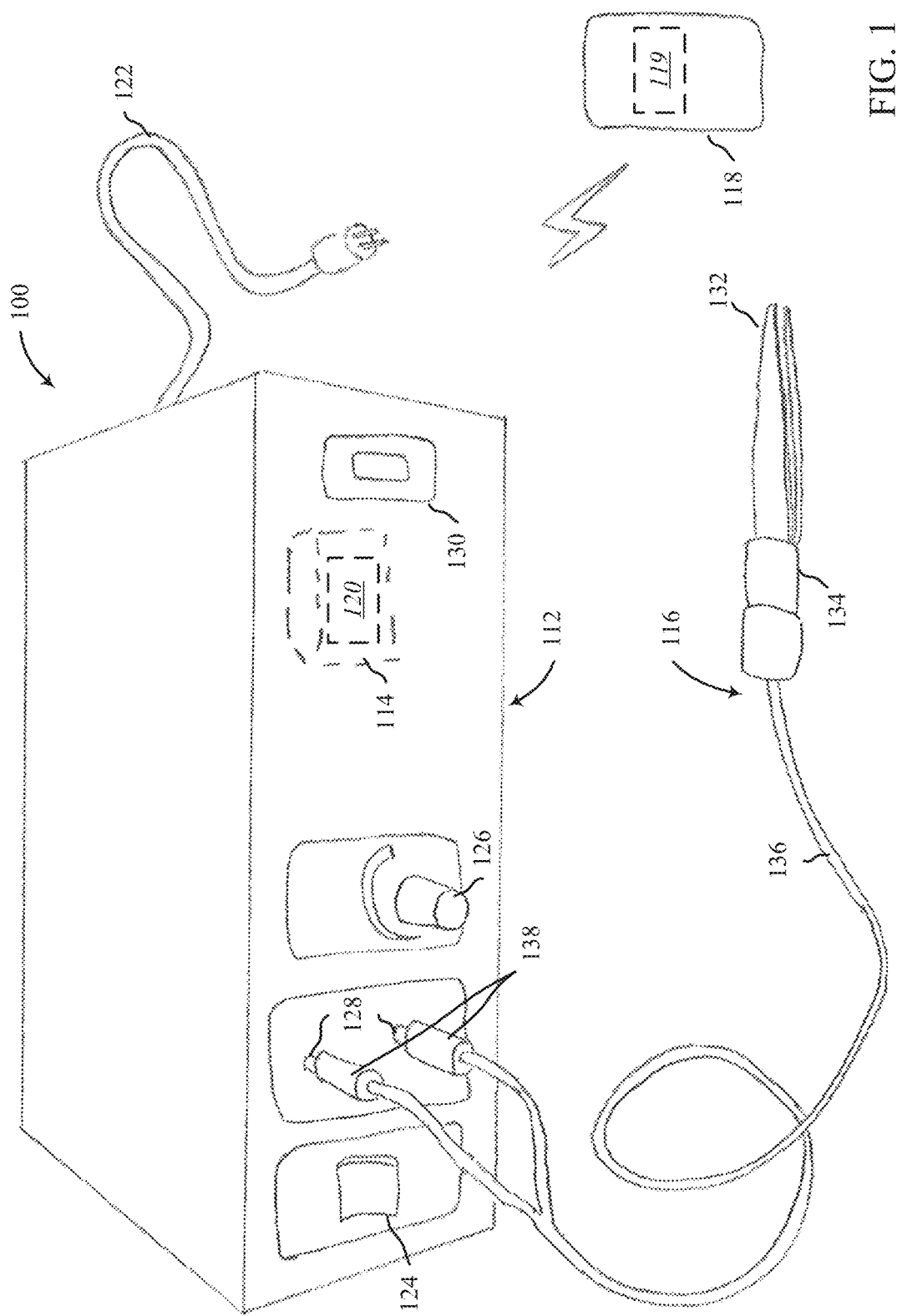
FIG. 1 is a perspective view of an example wireless surgical cautery device in accordance with this disclosure.

This description provides examples, and is not intended to limit the scope, applicability or configuration of the invention. Rather, the ensuing description will provide those skilled in the art with an enabling description for implementing embodiments of the invention. Various changes may be made in the function and arrangement of elements.

Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, devices, and software may individually or collectively be components of a larger system, wherein other procedures may take precedence over or otherwise modify their application.

The present disclosure is directed to surgical cautery devices and related methods of use. In particular, the present disclosure is directed to a surgical cautery device that is controlled wirelessly. The wireless control may involve actuation by a surgeon from a location remote from the voltage generator that provides power to the forceps or pin used to cauterize tissue. In one example, the actuator is included in footwear or related foot-worn objects such as socks, the insole of a shoe, or some other portion of a footwear. The wireless technology is particularly useful for bipolar surgical cautery devices, although the wireless capabilities may be generally applicable to various other types of cautery devices and other types of devices used in an operating room.

As noted above, it is typical for a foot pedal to be used for surgical cautery devices wherein the foot pedal is connected to a voltage generator with a wired connection. The operator may actuate the foot pedal to control power supply to forceps or other cautery instruments that are also connected to the voltage generator with a wired connection. In some types of procedures, the surgeon must move around the patient such as from one side of an operating table to another. The foot pedal must also be moved to provide access by the surgeon. This requirement for the foot pedal to be moved results in lost time, inefficiencies and distractions during the course of the medical procedure. Furthermore, the foot pedal may interfere with cushioned floor mats used around the operating room.

One advantage associated with the disclosed surgical cautery devices is that the actuator, rather than be positioned in a foot pedal that must be maneuvered around the operating room where the surgeon is located, may be mounted to the surgeon so as to move with him. Alternatively, multiple actuators may be positioned throughout the operating room, such as at standard locations where the surgeon may move around the patient during the course of a medical procedure. The actuator may be positioned in the shoe worn by the surgeon so as to be operated by some portion of the surgeon's foot. Alternatively, the actuator can be positioned within or on a cushioned floor mat and configured to be activated by the user's footwear. In other arrangements, the actuator may be positioned at other locations such as associated with the operating table where the surgeon can activate the actuator with his foot, knee, thigh, elbow, forearm, or other body part. In still further arrangements, the actuator may be integrated in or mounted to the forceps or other cauterizing instrument. In still further arrangements, the actuator may be integrated into a device worn at or around the surgeon's head, neck or shoulders and actuated using other parts of the surgeon's body such as the chin, shoulder, tongue, forehead or nose. Preferably, the actuator is operable in such a way that the surgeon does not have to use or move one of his hands or portions of the hand in order to actuate the cautery device such that the surgeon's hands remain free to hold other instruments and perform other tasks associated with the medical procedure.

Referring now to FIG. 1, an example surgical cautery device 100 is shown and described. The surgical cautery device 100 includes a voltage generator 112, a controller 114, forceps 116, an actuator 118, a transmitter 119, a receiver 120, and a power cord 122 with associated plug. The forceps 116 may be connected to the voltage generator 112 with a wired connection. The actuator 118 and transmitter 119 may be connected to the voltage generator 112 or components thereof (e.g., controller 114) with a wireless connection.

Eliminating the wired connection between the actuator 118 and the voltage generator 112 may provide a number of advantages as discussed herein. At least one such advantage includes the option of positioning the actuator 118 on the surgeon who is operating the cautery device 100, thus eliminating the need to separately move the actuator when the surgeon changes locations in the operating room. Another advantage relates to eliminating a set of wires on the floor, thus eliminating a potential tripping hazards.

The voltage generator 112 may include an on/off switch 124, a regulator 126, a pair of wire jacks 128, and a display 130. The voltage generator 112 may have any of a number of desired shapes, sizes, and configurations. The voltage generator 112 may include analogue and digital features. For example, the display 130 may be a digital display that indicates a voltage level or other indicator of power being applied to the forceps 116.

The entire voltage generator 112, or at least components thereof, may be integrated into other devices used in an operating room setting. The controller 114 may be integrated into the voltage generator 112 and connected to some or all of the features 124, 126, 128, 130. The receiver 120 may also be positioned in a housing of the voltage generator 112. The receiver 120 may be electrically connected to the controller 114. In some examples, the controller 114 includes the receiver 120 as a component thereof. The controller 114 may include other features and functionality as will be described below with reference to FIG. 6.

The forceps 116 may include cauterizing tips 132, a handle 134, wires 136, and wire plugs 138. The wire plugs may be connected to the wire jacks 128 of the voltage generator 112. The forceps 116 may include cauterizing tips 132 having different shapes, sizes and configurations. For example, the cauterizing tips 132 may have a tweezershaped construction. In other examples, the cauterizing tips 132 may include a pen-like structure.

The actuator 118 may be mobile relative to the voltage generator 112 and forceps 116. For example, the actuator 118 may be moveable relative to the voltage generator 112 without a wired connection. The actuator 118 may be mounted to or carried by the surgeon. In other arrangements, the actuator 118 may be positioned at other locations such as, for example, embedded in or positioned on a floor mat for use in the operating room. The actuator 118 may be positioned on the operating table, a stand intended to be positioned adjacent to the operating table, or on the patient himself.

The actuator 118 may include an on/off switch device that creates an on/off signal which is sent wirelessly to the controller 114 for controlling power to the forceps 116. The transmitter 119 may be electrically connected to the actuator 118 and configured to transmit the on/off signal to the controller 114 (i.e., via the receiver 120). In other arrangements, the actuator 118 has multiple signal generator capabilities. For example, in addition to an on/off switch that generates an on/off signal, the actuator 118 may include functionality to create a signal that incrementally raises or lowers the power supply to the forceps 116 while power is being supplied to the forceps 116 (i.e., when the power supply is in an "on" state). In one example, separate actuators 118 are provided for each individual function. Each of the actuators may be positioned within a common housing or may be separate from each other. For example, one actuator 118 may be positioned in one shoe of the surgeon to create an on/off signal, and another actuator may be positioned in an opposite shoe of the surgeon to provide adjustability of the power supply to the forceps 116. In another embodiment, both actuators are positioned in the same shoe and positioned to be actuated by separate toes of the operator. Each actuator 118 may have a transmitter 119 associated therewith, or may use a single transmitter depending on the physical location and configuration for the actuators 118. Many other numbers of actuators and arrangements for the actuators may be possible.

Figure 2:
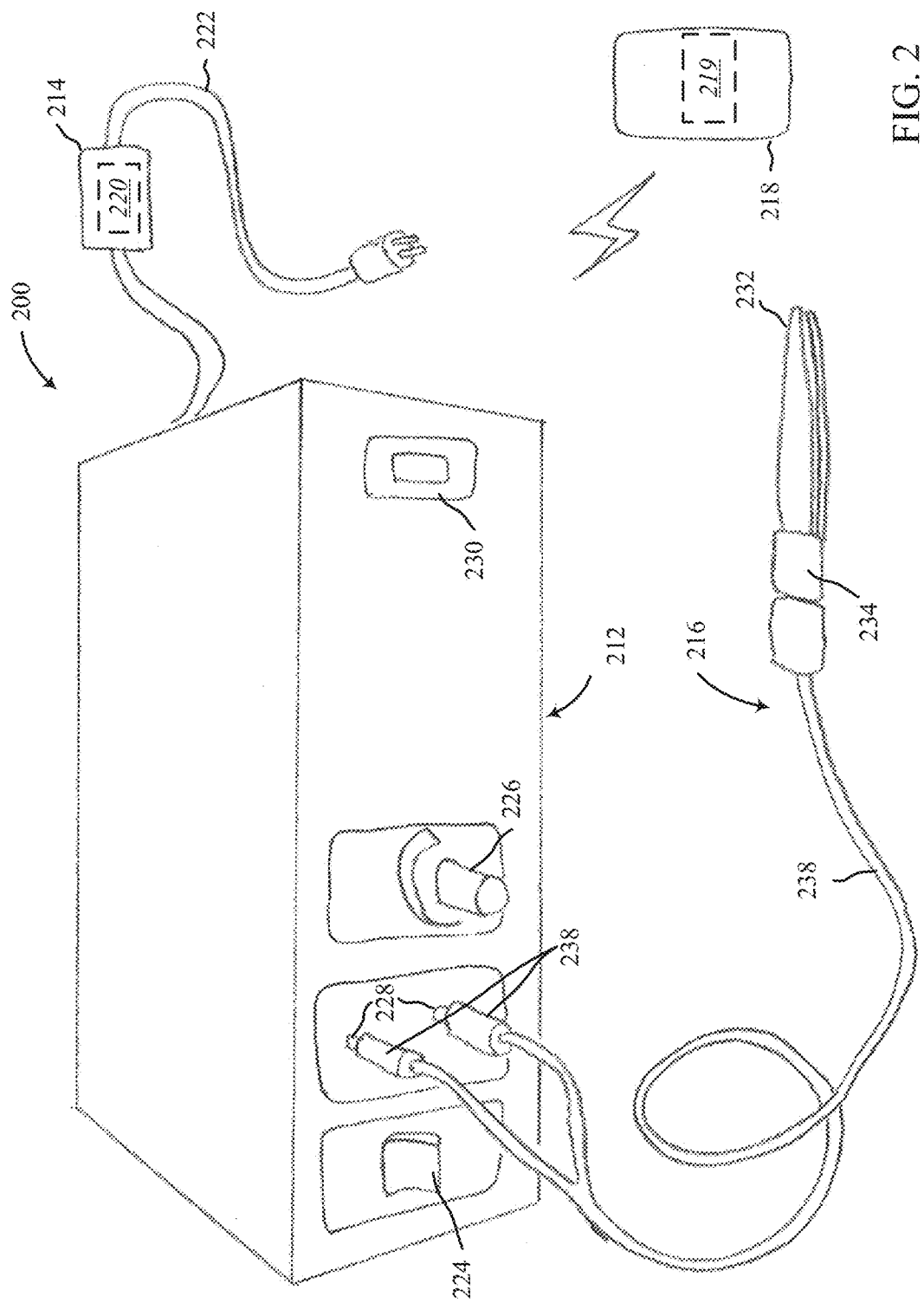
FIG. 2 is a perspective view of another example wireless surgical cautery device in accordance with this disclosure.

FIG. 2 illustrates another example surgery cautery device 200 that includes a voltage generator 212, a controller 214, forceps 216, an actuator 218, a transmitter 219, a receiver 220, and a power cord 222 having a plug. The voltage generator 212 may include an on/off switch 224, a regulator 226, wire jacks 228, and a display 230. The forceps 216 may include cauterizing tips 232, a handle 234, a wire 236, and wire plugs 238. Generally, the cautery device 200 includes many of the same or similar features as set forth above and described with reference to the surgical cautery device 100 of FIG. 1.

The controller 214 may be positioned within the power cord 222 and/or electrically coupled between the power cord 22 and the voltage generator 212. The receiver 220 may be housed with the controller 214 and/or may be part of the controller 214. The controller 214 may operate to control power supply to the entire voltage generator 212 as a master on/off switch. This configuration may be particularly effective if retrofitting an existing surgical cautery device with a wirelessly controlled power supply. The surgical cautery device 100 shown in FIG. 1 may require additional modifications to provide the wireless power control feature for the surgical cautery device. The surgical cautery device 100 may have advantages as compared to the surgical cautery device 200 in that it may be positioned and operable to control power supplied to the forceps 116 only rather than to the entire surgical cautery device as with the embodiment of FIG. 2.

Figure 3A:
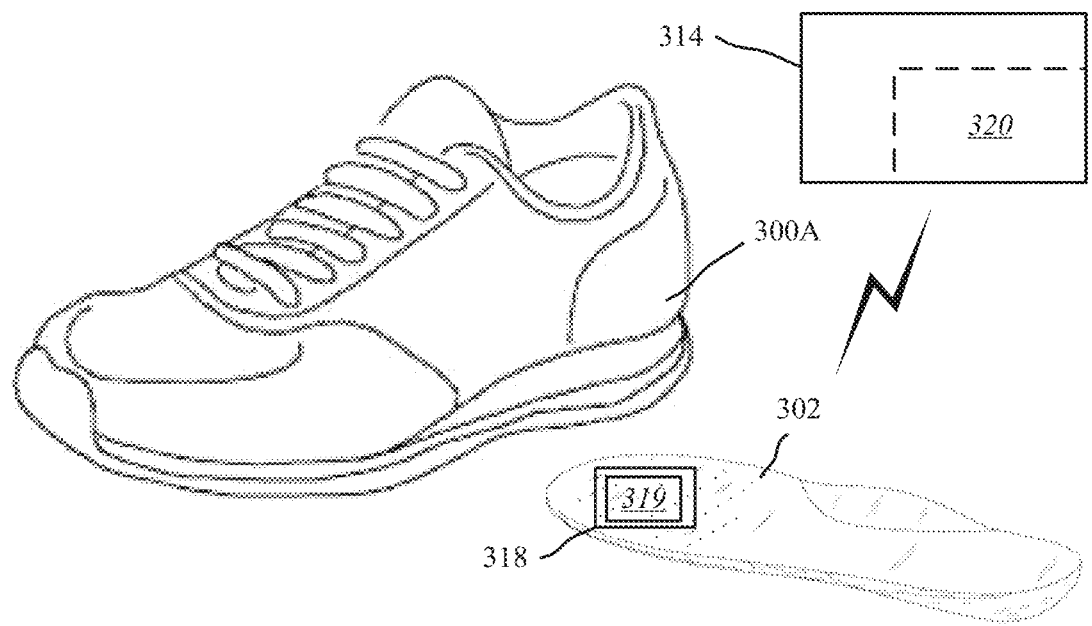
FIG. 3A is a perspective view of a footwear having a cautery device actuator in accordance with this disclosure.

FIG. 3A illustrates a shoe 300A having an insole 302 to which is mounted an actuator 318 having a transmitter 319. The actuator and/or transmitter 318, 319 may be integrated into the insole 302, or mounted to a surface of the insole 302, such as a detachable connection to a top surface of the insole 302. With the insole 302 inserted into the interior of the shoe 308, a surgeon may mount the shoe to his foot and use a portion of the foot (e.g., the toes) to actuate the actuator 318. In one example, the actuator may be an on/off switch that generates an on/off signal, and the transmitter 319 wirelessly transmits the on/off signal to a receiver 320 and controller 314 at a remote location (e.g., as described above for the surgical cautery devices 100, 200).

Figure 3B:
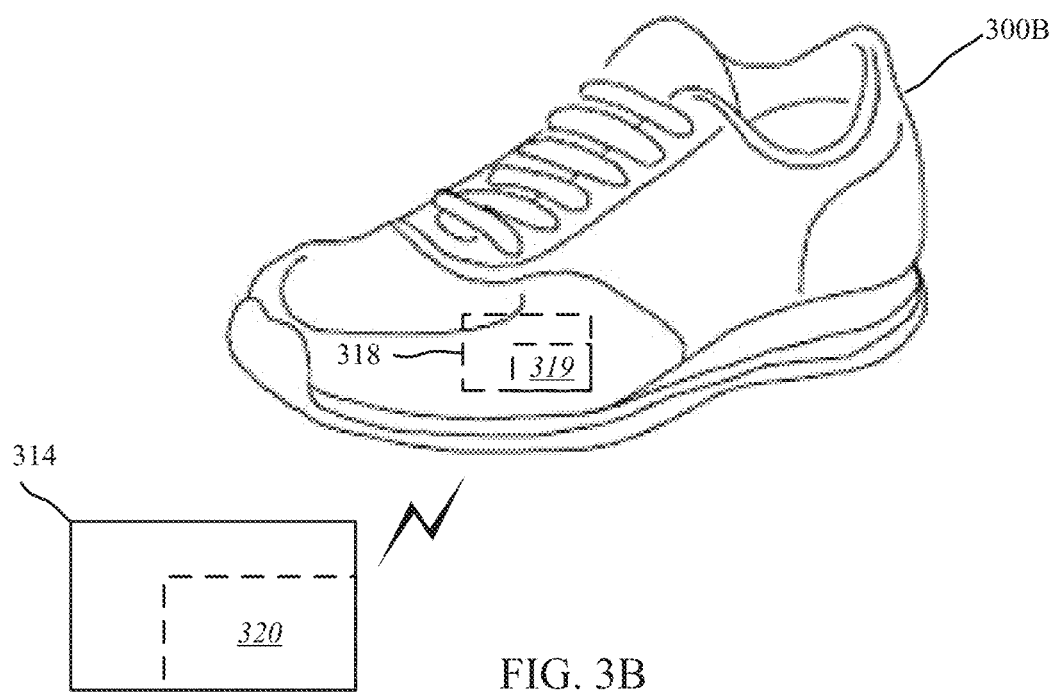
FIG. 3B is a perspective view of a footwear and footwear insole having a cautery device actuator in accordance with this disclosure.

FIG. 3B illustrates a shoe 300B that includes the actuator 318 and transmitter 319 integrated into the shoe 300B. The actuator 318 and transmitter 319 may be positioned in an upper portion of the shoe 300B, a sole structure of the shoe 300B, or elsewhere. Typically the actuator 318 is arranged to be actuated by a portion of the user's foot such as, for example, the toe, heel or ball of the foot. The actuator 318 generates a signal that is transmitted wirelessly by the transmitter 319 to a receiver 320 of a controller 314. The receiver 320 and controller 314 may be associated with any desired medical device, such as the surgical cautery device 100, 200 described above.

Figure 4:
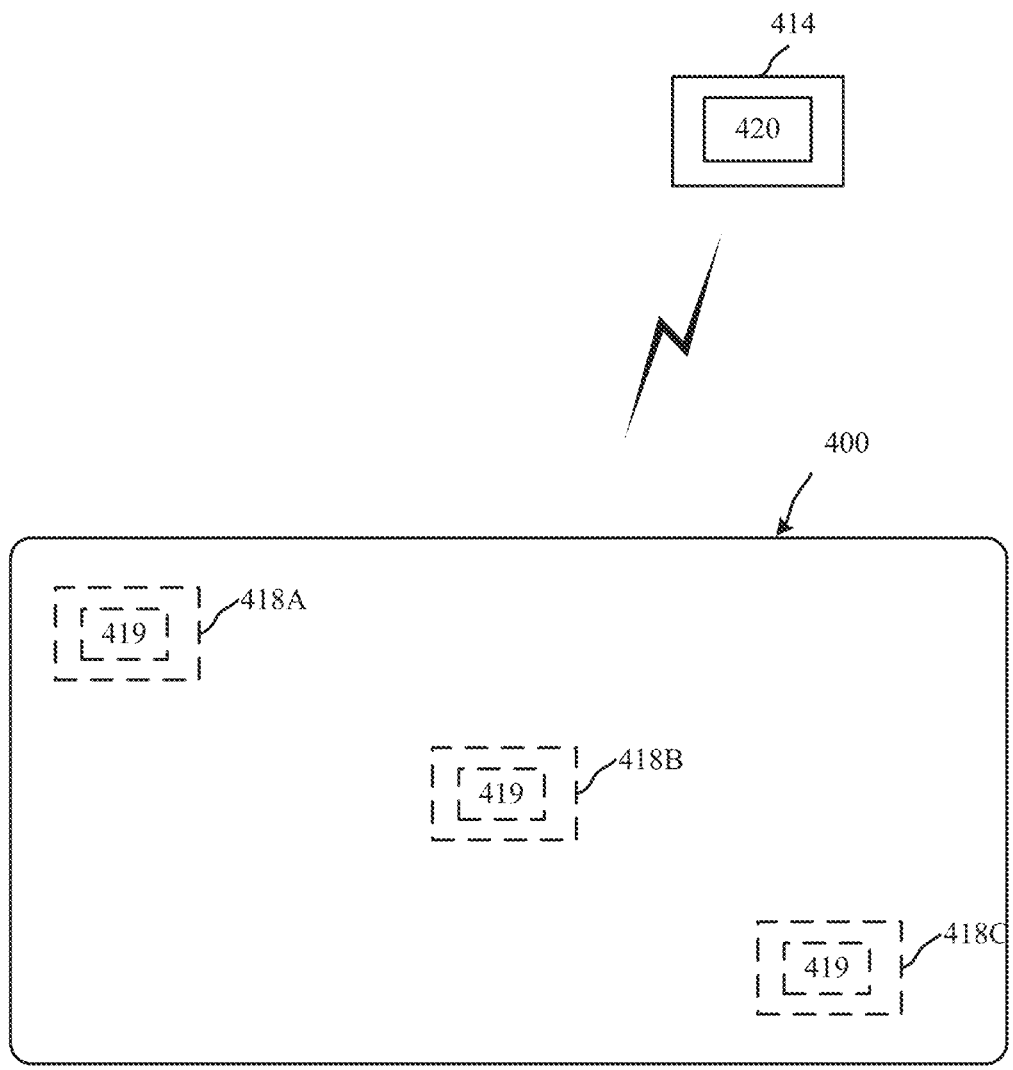
FIG. 4 illustrates a floor mat having at least one cautery device actuator in accordance with this disclosure.

FIG. 4 illustrates a floor mat 400 that includes multiple actuators 418A, 418B, 418C with associated transmitters 419. The actuators 418A-C may be embedded in a structure of the mat 400. Alternatively, the actuators 418A-C may be positioned on a bottom side surface or a top side surface, or positioned between layers of the mat 400. Although multiple actuators 418 are shown, other embodiments are possible that include a single actuator located at any desired location on the mat 400. The actuator 418 may be positioned at locations where a surgeon typically stands relative to an operating table or relative to a patient's body during a medical procedure. Multiple actuators may be positioned on the mat, or multiple mats each including one or more actuators, so as to position actuators at desired locations around the operating room. The actuator 418A-C may operate to generate a signal that is transmitted by the transmitter 419 to a receiver 420 of a controller 414. The signal generated by the actuator 418 may be an on/off signal or any other desired control signal for operation of a medical device such as the surgical cautery devices 100, 200 described herein.

Figure 5:
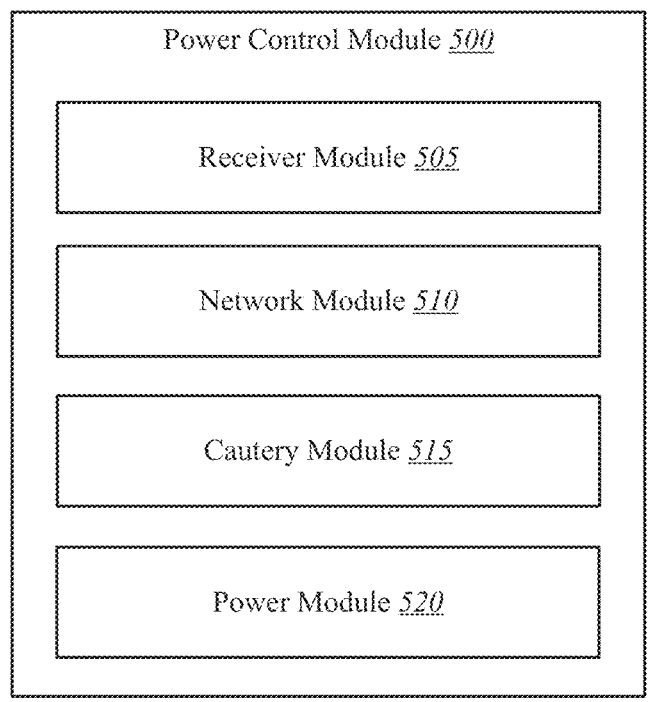
FIG. 5 is a block diagram of one or more modules in accordance with various aspects of this disclosure.

FIG. 5 shows a block diagram of a power control module 500. The power control module 500 may include one or more processors, memory, and/or one or more storage devices. The power control module 500 may include receiver module 505, network module 510, cautery module 515 and power module 520. Modules shown in FIG. 5 may each be in communication with each other. Modules shown in FIG. 5 may perform at least one of the operations described herein in conjunction with one or more controllers, transmitters, receivers, or other features of a voltage generator or other medical device.

The receiver module 505 may operate to receive signals from the actuator and/or transmitters described herein. In some examples, the receiver module 505 may receive wireless communication signals such as those wireless communication signals described below with reference to the system 600 of FIG. 6. The receiver module 505 may be closely interrelated with the receivers of the surgical cautery devices and actuator devices disclosed herein.

The network module 510 may operate to communicate with a network to connect the surgical cautery devices disclosed herein with a broader network, such as a hospital communications network or a closed network for an operating room. The network module 510 may operate with a wired connection or through a wireless communication system. The network module 510 may communicate information related to operation of the surgical cautery devices disclosed herein, store data, provide a communication system for downloading software, firmware or other updates to the surgical cautery device, and the like.

Cautery module 515 may control and/or monitor power supply to the forceps of a surgical cautery device. The cautery module 515 may monitor various signals such as on/off signals and power control signals received from an actuator via transmitter and associated wireless communications as described above. The cautery module 515 may be adapted to communicate with a variety of different cautery instruments such as the forceps disclosed herein, a pen-like device, or the like.

The power module 520 may have different features and functionality depending on the configuration of the surgical cautery device. For example, the power module 520 may regulate power to the entire surgical cautery device if the controller is positioned in the power cord as shown in FIG. 2 as compared to internal the voltage generator as described with reference to FIG. 1. The power module 520 may allocate power to various features and functionality of the voltage generator or other features of the surgical cautery device besides the forceps alone.

Figure 6:
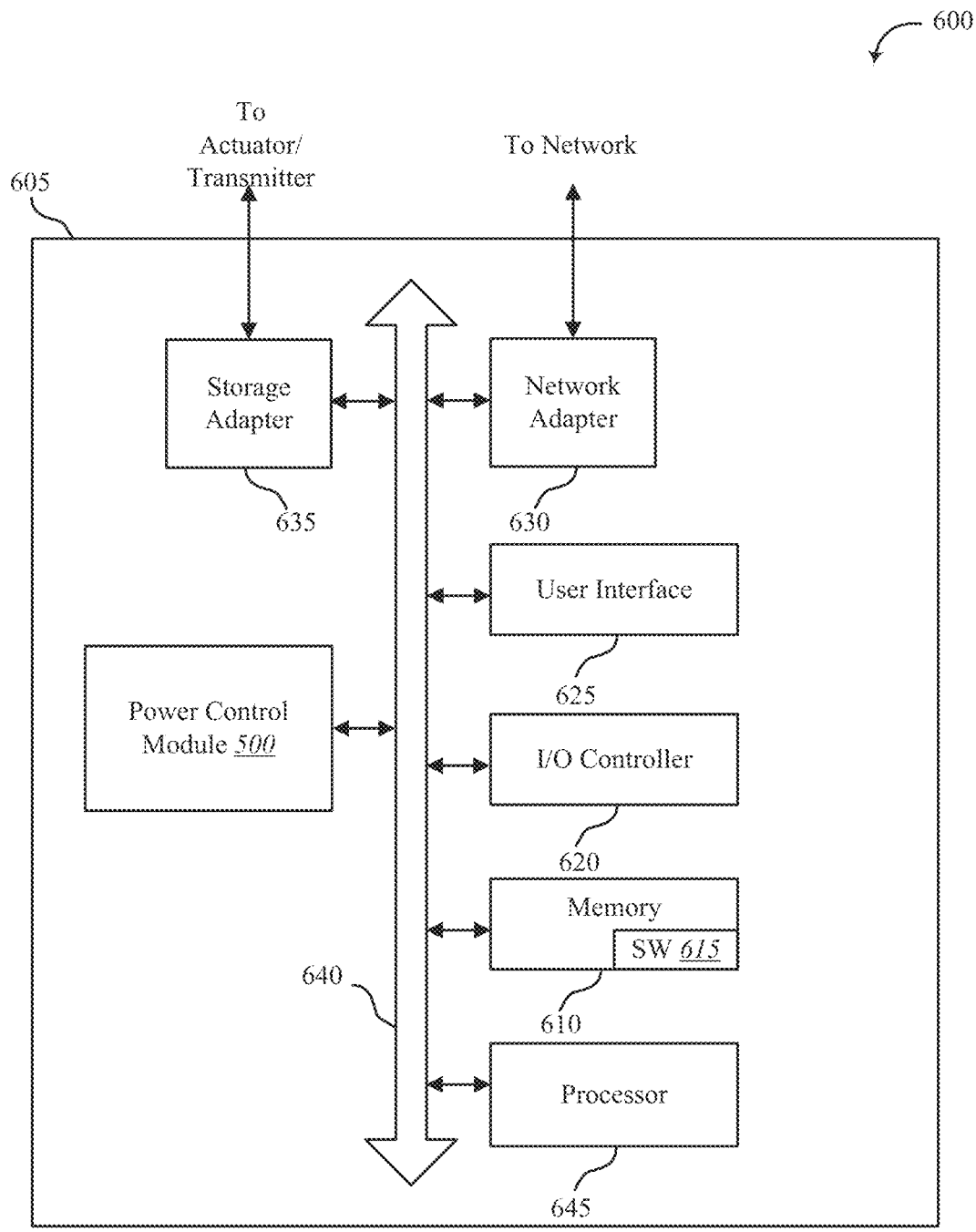
FIG. 6 is one embodiment of an environment in accordance with various aspects of this disclosure.

FIG. 6 shows a surgical cautery system 600. System 600 may include an apparatus 605, which may be an example of any one of device 100 of FIG. 1, apparatus 200 of FIG. 2, devices 300A, 300B of FIGS. 3A and 3B, the device 400 of FIG. 4, and/or the module 500 of FIG. 5.

Apparatus 605 may include components for wireless control of a surgical cautery device and related communications including components for transmitting communications and components for receiving communications. For example, apparatus 605 may communicate bi-directionally with one or more actuators and/or transmitters, and a network, such as a hospital data network. These bi-directional communications may be direct (apparatus 605 communicating directly with an actuator/transmitter or network, for example) and/or indirect (apparatus 605 communicating indirectly with another device through a server, for example).

Apparatus 605 may also include a processor module 645, memory 610 (including software/firmware code (SW) 615), an input/output controller module 620, a user interface module 625, a network adapter 630, and a storage adapter 635. The software/firmware code 615 may be one example of a software application executing on apparatus 605. The network adapter 630 may communicate bi-directionally, via one or more wired links and/or wireless links, with one or more networks and/or client devices. In some embodiments, network adapter 630 may provide a direct connection to a client device via a direct network link to the Internet via a POP (point of presence). In some embodiments, network adapter 630 of apparatus 605 may provide a connection using wireless techniques, including digital cellular telephone connection, Cellular Digital Packet Data (CDPD) connection, digital satellite data connection, and/or another connection. The apparatus 605 may include power control module 500, which may perform the functions described above for the power control module 500 of FIG. 5.

The signals associated with system 600 may include wireless communication signals such as radio frequency, electromagnetics, local area network (LAN), wide area network (WAN), virtual private network (VPN), wireless network (using 802.11, for example), cellular network (using 3G and/or LTE, for example), and/or other signals. The network adapter 630 may enable one or more of WWAN (GSM, CDMA, and WCDMA), WLAN (including BLUETOOTH® and Wi-Fi), WMAN (WiMAX) for mobile communications, antennas for Wireless Personal Area Network (WPAN) applications (including RFID and UWB), or any combination thereof. Such wireless communications signals may be used with any of the devices and systems disclosed herein, such as the surgical cautery devices 100, 200.

One or more buses 640 may allow data communication between one or more elements of apparatus 605 such as processor module 645, memory 610, I/O controller module 620, user interface module 625, network adapter 630, and storage adapter 635, or any combination thereof.

The memory 610 may include random access memory (RAM), read only memory (ROM), flash memory, and/or other types. The memory 610 may store computer-readable, computer-executable software/firmware code 615 including instructions that, when executed, cause the processor module 645 to perform various functions described in this disclosure. Alternatively, the software/firmware code 615 may not be directly executable by the processor module 645 but may cause a computer (when compiled and executed, for example) to perform functions described herein. Alternatively, the computer-readable, computer-executable software/firmware code 615 may not be directly executable by the processor module 645, but may be configured to cause a computer, when compiled and executed, to perform functions described herein. The processor module 645 may include an intelligent hardware device, for example, a central processing unit (CPU), a microcontroller, an application-specific integrated circuit (ASIC), field programmable gate array (FPGA), or any combination thereof.

In some embodiments, the memory 610 may contain, among other things, the Basic Input-Output system (BIOS) which may control basic hardware and/or software operation such as the interaction with peripheral components or devices. For example, at least a portion of the power control module 500 to implement the present systems and methods may be stored within the system memory 610. Applications resident with system 600 are generally stored on and accessed via a non-transitory computer readable medium, such as a hard disk drive or other storage medium. Additionally, applications can be in the form of electronic signals modulated in accordance with the application and data communication technology when accessed via a network interface such as network adapter 630.

Many other devices and/or subsystems may be connected to and/or included as one or more elements of system 600 (for example, a personal computing device, mobile computing device, smart phone, server, internet-connected device, cell radio module, or any combination thereof). In some embodiments, all of the elements shown in FIG. 6 need not be present to practice the present systems and methods. The devices and subsystems can be interconnected in different ways from that shown in FIG. 6. In some embodiments, an aspect of some operation of a system, such as that shown in FIG. 6, may be readily known in the art and are not discussed in detail in this application. Code to implement the present disclosure can be stored in a non-transitory computer-readable medium such as one or more of system memory 610 or other memory. The operating system provided on I/O controller module 620 may be a mobile device operation system, a desktop/laptop operating system, or another known operating system.

The I/O controller module 620 may operate in conjunction with network adapter 630 and/or storage adapter 635. The network adapter 630 may enable apparatus 605 with the ability to communicate with devices such as devices 100 and 118 of FIG. 1, and/or other devices over a communication network. Network adapter 630 may provide wired and/or wireless network connections. In some cases, network adapter 630 may include an Ethernet adapter or Fibre Channel adapter. Storage adapter 635 may enable apparatus 605 to access one or more data storage devices such as storage media 110. The one or more data storage devices may include two or more data tiers each. The storage adapter 635 may include one or more of an Ethernet adapter, a Fibre Channel adapter, Fibre Channel Protocol (FCP) adapter, a SCSI adapter, and iSCSI protocol adapter.

Figure 7:
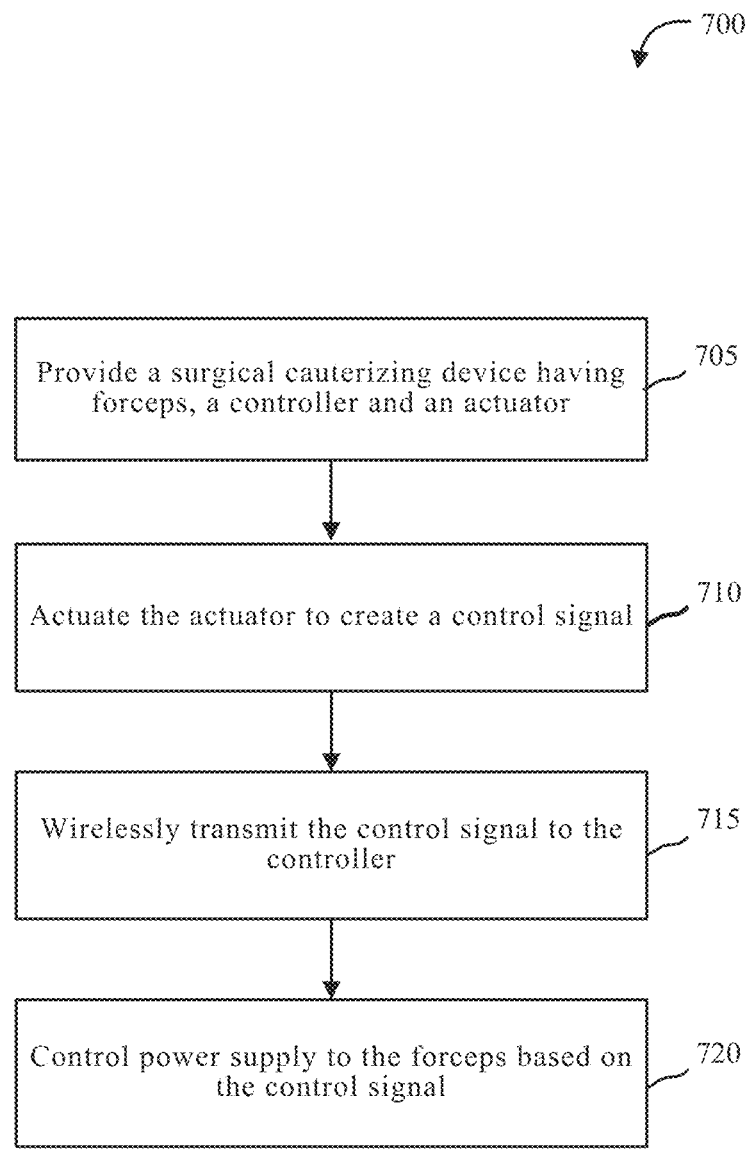
FIG. 7 is a flow diagram showing steps of an example method of operating a wireless surgical cautery device in accordance with the present disclosure.

FIG. 7 is a flow diagram showing steps of an example method 700 of operating a surgical cautery apparatus. The method 700 may be applicable to any of the devices and systems disclosed herein, individually or in combination, such as the device 100 of FIG. 1, apparatus 200 of FIG. 2, devices 300A, 300B of FIGS. 3A and 3B, the device 400 of FIG. 4, the module 500 of FIG. 5, and/or the system 600 of FIG. 6.

The method 700 includes, at block 705, a step of providing a surgical cautery device having forceps, a controller, and an actuator. The forceps may be any desired instrument for conducting cautery of tissue. At block 710, the method 700 includes actuating the actuator to create and control signal. Block 715 includes wirelessly transmitting the control signal to the controller. Method 700 further includes, at block 720, controlling power supply to the forceps based on the control signal. The actuator may be positioned in a user's shoe, and actuating the actuator may include manipulating a portion of the user's foot. The actuator may be positioned in a floor mat, and actuating the actuator may include manipulating a portion of the user's foot that is supported on the floor mat. The surgical cautery device may further include a voltage generator, and controlling the power supply to the forceps may include operating the voltage generator with the controller.

The description herein provides examples, and is not limiting of the scope, applicability, or examples set forth in the claims. Changes may be made in the function and arrangement of elements discussed without departing from the scope of the disclosure. Various examples may omit, substitute, or add various procedures or components as appropriate. Also, features described with respect to some examples may be combined in other examples.

The description set forth herein, in connection with the appended drawings, describes example configurations and does not represent all the examples that may be implemented or that are within the scope of the claims. The term "exemplary" as may be used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (e.g., A and B and C).

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed herein.

What is claimed is:

1. A surgical cautery device, comprising:
   a voltage generator configured to be electrically connected to a power source;
   a controller;
   forceps electrically coupled to the voltage generator and configured to cauterize tissue;
   an actuator configured to generate and wirelessly transmit an on/off signal;
   a power cable that extends from the power source to the voltage generator; and
   a receiver positioned in the power cable, wherein said receiver is operable to wirelessly receive the on/off signal, the controller configured to control power to the voltage generator from the power source in response to the on/off signal.

2. The surgical cautery device of claim 1, wherein the actuator is an on/off switch.

3. The surgical cautery device of claim 1, wherein the actuator is embedded in a shoe.

4. The surgical cautery device of claim 1, wherein the actuator is embedded in a removable shoe insole.

5. The surgical cautery device of claim 1, wherein the actuator is embedded in a floor mat.

6. The surgical cautery device of claim 1, wherein the on/off signal is transmitted wirelessly.

7. The surgical cautery device of claim 1, further comprising a housing, the voltage generator and controller being positioned in the housing.

8. A surgical cautery device comprising:
   a controller;
   forceps configured to cauterize tissue;
   an actuator configured to wirelessly transmit an on/off signal;
   a receiver positioned in a power cable that extends from a power source to a voltage generator, said receiver being operable to wirelessly receive the on/off signal, the controller configured to control power to the forceps in response to the on/off signal.

9. The surgical cautery device of claim 8, wherein the actuator is positioned in a shoe of a user and is operable by movement of one or more toes of the user.

10. The surgical cautery device of claim 8, wherein the actuator is positioned in a floor mat.

11. The surgical cautery device of claim 8, wherein the forceps is electrically coupled to the voltage generator, and the controller is configured to control the voltage generator to control power to the forceps.

12. A surgical cautery device comprising:
a controller;
forceps configured to cauterize tissue;
an actuator configured to transmit a control signal, the actuator being positioned in a shoe of a user and is operable with a portion of a foot of the user;
wherein the controller is configured to receive the control signal from the actuator using a receiver positioned in a power cable that extends from a power source to a voltage generator, and to control power to the forceps in response to the control signal.

13. The surgical cautery device of claim 12, wherein the actuator is configured to transmit the control signal wirelessly, and the controller receives the control signal wirelessly.

14. The surgical cautery device of claim 12, wherein the actuator is configured to transmit the control signal wirelessly.

15. The surgical cautery device of claim 12, wherein the forceps is electrically coupled to the voltage generator, and the controller is configured to control the voltage generator to control power to the forceps.

16. A method of operating a surgical cautery device having forceps, comprising:
providing the surgical cauterizing device having forceps, a controller and an actuator;
actuating the actuator to create a control signal;
wirelessly transmitting the control signal to the controller using a receiver positioned in a power cable that provides power to the cauterizing device;
controlling power to the forceps based on the control signal, wherein the power cable extends from a power supply to a voltage generator.

17. The method of claim 16, wherein the actuator is positioned in a shoe of a user, and actuating the actuator includes manipulating a portion of a foot of the user.

18. The method of claim 16, wherein the actuator is positioned in a floor mat, and actuating the actuator includes manipulating a portion of a user's foot that is supported on the floor mat.

19. The method of claim 16, wherein controlling the power to the forceps includes operating the voltage generator with the controller.

* * * * *